(12) United States Patent  
Liddy et al.

(10) Patent No.: US 9,427,303 B2
(45) Date of Patent: Aug. 30, 2016

(54) ANTI-ASPIRATION VALVE

(71) Applicant: Cook Medical Technologies LLC, Bloomington, IN (US)

(72) Inventors: Alison Liddy, Salthill (IE); John Neilan, Gort (IE); Michael Ryan, Dooradoyle (IE); Gerard Treacy, Castletroy (IE)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/794,010

(22) Filed: Mar. 11, 2013

(65) Prior Publication Data

US 2013/0289711 A1  Oct. 31, 2013

Related U.S. Application Data

(60) Provisional application No. 61/639,221, filed on Apr. 27, 2012.

(51) Int. Cl.
*A61F 2/06* (2013.01)
*A61F 2/04* (2013.01)
(Continued)

(52) U.S. Cl.
CPC ... *A61F 2/06* (2013.01); *A61F 2/04* (2013.01); *A61F 2/07* (2013.01); *A61F 2/2412* (2013.01); *A61F 2/2415* (2013.01); *A61F 2002/044* (2013.01)

(58) Field of Classification Search
CPC .............. A61F 2/04; A61F 2/06; A61F 2/07; A61F 2/2412; A61F 2/2418; A61F 2/2475; A61F 2002/044; A61F 2/02; A61F 2/24; A61F 2/2415

USPC ............ 623/23.68, 1.24, 23.64, 23.65, 23.66, 623/23.67, 23.69, 23.7, 1.23, 1.26, 2.1, 623/2.12, 2.16, 2.17, 2.18
See application file for complete search history.

(56) References Cited

U.S. PATENT DOCUMENTS 4,434,810 A  3/1984  Atkinson
4,846,836 A  7/1989  Reich
(Continued)

FOREIGN PATENT DOCUMENTS

EP   1 430 853 B1   6/2004
EP   1 704 834 B1   9/2006
(Continued)

OTHER PUBLICATIONS www.thefreedictionary.com—http://www.thefreedictionary.com/atmospheric+pressure.*
(Continued)

*Primary Examiner* — Christopher D Prone
*Assistant Examiner* — Rokhaya Diop
(74) *Attorney, Agent, or Firm* — Brinks Gilson & Lione (57) ABSTRACT

A prosthesis and a method for making a prosthesis for controlling flow through a bodily lumen are provided. The prosthesis includes a body having a proximal portion, a distal portion and a lumen extending therethrough and further includes a valve operably connected to the body. The valve has a distal end including a first portion of a surface of the valve lumen and a second portion of the surface that contact each other and form a seal in a closed configuration. The distal end of the valve is formed such that the first portion and the second portion of the surface of the valve lumen contact each other and the distal end is configured to open in response to a pressure that is greater than atmospheric pressure.

13 Claims, 11 Drawing Sheets

(51) Int. Cl.
*A61F 2/24* (2006.01)
*A61F 2/07* (2013.01)

(56) References Cited

U.S. PATENT DOCUMENTS

| | | | |
|---|---|---|---|
| 5,314,473 | A * | 5/1994 | Godin ..................... 623/23.68 |
| 5,392,775 | A | 2/1995 | Adkins, Jr. et al. |
| 5,861,036 | A | 1/1999 | Godin |
| 6,264,700 | B1 | 7/2001 | Kilcoyne et al. |
| 6,302,917 | B1 | 10/2001 | Dua et al. |
| 6,544,291 | B2 | 4/2003 | Taylor |
| 6,746,489 | B2 | 6/2004 | Dua |
| 6,790,237 | B2 * | 9/2004 | Stinson .................. 623/23.68 |
| 7,118,600 | B2 | 10/2006 | Dua et al. |
| 7,182,788 | B2 | 2/2007 | Jung et al. |
| 7,354,455 | B2 | 4/2008 | Stinson |
| 7,993,410 | B2 | 8/2011 | Shin et al. |
| 8,029,557 | B2 | 10/2011 | Sobrino-Serrano et al. |
| 8,221,505 | B2 | 7/2012 | Skerven |
| 2003/0040808 | A1 | 2/2003 | Stack et al. |
| 2004/0102855 | A1 | 5/2004 | Shank |
| 2005/0137681 | A1 | 6/2005 | Shoemaker et al. |
| 2007/0213813 | A1 | 9/2007 | Von Segesser et al. |
| 2008/0086214 | A1 | 4/2008 | Hardin et al. |
| 2008/0275548 | A1 * | 11/2008 | Svensson .................. 623/2.1 |
| 2009/0138071 | A1 | 5/2009 | Cheng et al. |
| 2009/0171447 | A1 | 7/2009 | Von Segesser et al. |
| 2010/0036504 | A1 | 2/2010 | Sobrino-Serrano et al. |
| 2010/0114327 | A1 | 5/2010 | Sobrino-Serrano |
| 2010/0121461 | A1 | 5/2010 | Sobrino-Serrano et al. |
| 2010/0121462 | A1 | 5/2010 | Sobrino-Serrano et al. |
| 2010/0137998 | A1 * | 6/2010 | Sobrino-Serrano et al. ..................... 623/23.68 |
| 2011/0160836 | A1 | 6/2011 | Behan |
| 2011/0190905 | A1 | 8/2011 | Behan |
| 2012/0059486 | A1 | 3/2012 | Sobrino-Serrano et al. |
| 2012/0158026 | A1 | 6/2012 | Behan |
| 2012/0197386 | A1 | 8/2012 | Von Segesser et al. |

FOREIGN PATENT DOCUMENTS

| | | |
|---|---|---|
| EP | 1 952 785 B1 | 8/2008 |
| EP | 2 248 486 A2 | 11/2010 |
| EP | 2 316 381 A2 | 5/2011 |
| EP | 2 368 527 A1 | 9/2011 |
| EP | 2 387 973 A1 | 11/2011 |
| GB | 1 354 691 A | 5/1974 |
| WO | WO 03/030782 A1 | 4/2003 |
| WO | WO 2006/004679 A1 | 1/2006 |
| WO | WO 2008/028569 A1 | 3/2008 |
| WO | WO 2011/073970 A1 | 6/2011 |

OTHER PUBLICATIONS

International Search Report mailed Aug. 19, 2013 for International Application No. PCT/US2013/037578.
Written Opinion of the International Searching Authority mailed Aug. 19, 2013 for International Application No. PCT/US2013/037578.

* cited by examiner

| Proximal End Formed Shape | Distal End Formed Shape |
|---|---|
|  |  |
|  |  |
|  |  |
|  |  |
|  |  |
|  |  |
|  |  |
|  |  |
|  |  |

ANTI-ASPIRATION VALVE

RELATED APPLICATIONS

This application claims the benefit of U.S. Provisional Application No. 61/639,221, filed Apr. 27, 2012, which is incorporated by reference herein in its entirety.

FIELD OF THE INVENTION

The present invention relates to medical devices and in particular to a valve for regulating fluid flow therethrough.

BACKGROUND OF THE INVENTION

The lower esophageal sphincter (LES) in healthy individuals allows food to pass into the stomach, but prevents gastric fluids from moving into the esophagus except when the patient vomits. Aspiration is a clinical risk for patients having a malfunctioning LES or for patients having stents placed across the gastroesophageal junction (GEJ) so that an opening is created at the bottom of the esophagus that can lead to acid reflux and aspiration. Aspiration occurs when the stomach contents travel from the stomach into the lungs. Aspiration in the lungs can lead to pneumonia or death. Risk of aspiration in patients having a compromised LES increases when the patient is in a prone position.

Anti-reflux esophageal prostheses or stents have been developed to treat tumors or strictures in the vicinity of the LES. Anti-reflux esophageal prosthesis or stent is typically placed in the lower esophagus and through the LES to maintain the patency thereof due to the presence of a cancerous tumor commonly found in the vicinity thereof or to treat benign tumor conditions, such as blockage or strictures.

A problem with an esophageal prosthesis or stent is that fluid from the stomach flows into the mouth of the patient when in a prone position, increasing the risk of aspiration. In an attempt to solve the problem, a number of esophageal prostheses or stents utilize a one-way valve such as a duck-bill or reed-type valve in which only food or fluid from the esophagus flows into the stomach in only an antegrade or forward direction. However, these one-way anti-reflux prostheses or stents present another problem. When the patient wants to belch or vomit, the patient is prevented from doing so, because the one-way valve prevents backward flow in the retrograde direction. Such condition is not only painful to the patient, but can also lead to more complicated medical conditions. Some esophageal prostheses or stents use a sleeve that extends into the stomach to control the flow of fluids. However, at standard pressure within the stomach, and in the absence of external pressure (i.e. standard temperature and pressure) such as when the patient is in the prone position, the sleeve may not seal to prevent reflux of the stomach contents into the mouth.

What is needed is a prosthesis that is normally closed to prevent gastric fluids from entering the esophagus even in the absence of external pressure within the stomach (i.e. at standard temperature and pressure), allows food to pass into the stomach and also allows for vomiting and belching when necessary and returns to the closed position.

BRIEF SUMMARY

Accordingly, it is an object of the present invention to provide a device and a method having features that resolve or improve on the above-described drawbacks.

A prosthesis and a method for making a prosthesis for controlling flow through a bodily lumen are provided. The prosthesis includes a body having a proximal portion, a distal portion and a lumen extending therethrough and further includes a valve operably connected to the body where the valve includes a proximal portion, a distal portion and a lumen extending through the valve. The valve lumen is operably connected to the body lumen. The valve has a distal end including a first portion of a surface of the valve lumen and a second portion of the surface that contact each other and form a seal in a closed configuration to prevent fluid from entering the distal end in a retrograde direction at standard atmospheric pressure. The distal end of the valve is formed such that the first portion and the second portion of the surface of the valve lumen contact each other and the distal end is configured to open in response to a pressure that is greater than atmospheric pressure.

DETAILED DESCRIPTION

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the prosthesis to a patient. Hence the term "distal" means the portion of the prosthesis that is farthest from the physician and the term "proximal" means the portion of the prosthesis that is nearest to the physician.

The present invention relates to medical devices, and in particular to prosthetic devices for implantation in a body lumen such as the lower esophageal sphincter or a vessel. As used herein, the term "implantable" refers to an ability of a medical device to be positioned at a location within a body, such as within a body lumen, either temporarily, semi-permanently, or permanently. Permanent fixation of the device in a particular position is not required. Furthermore, the terms "implantation" and "implanted" refer to the positioning of a medical device at a location within a body, such as within a body lumen.

Figure 1:
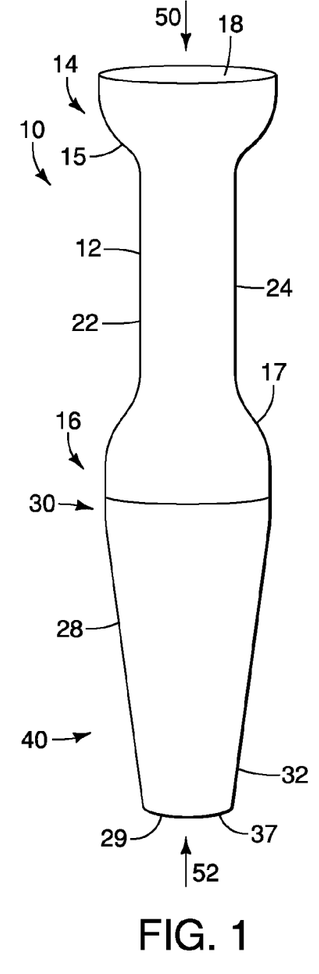
FIG. 1 is a front view of a prosthesis in accordance with an embodiment of the present invention.
Figure 2:
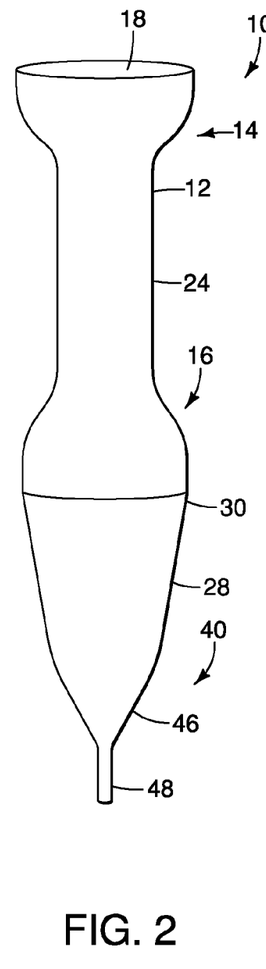
FIG. 2 is a side view of the embodiment shown in FIG. 1.

FIGS. 1 and 2 illustrate a prosthesis 10 in accordance with an embodiment of the present invention. FIG. 1 illustrates a front view of the prosthesis 10 and FIG. 2 illustrates a side view of the embodiment shown in FIG. 1. The prosthesis 10 includes a body 12 having proximal portion 14, a distal portion 16 and a lumen 18 extending therethrough. In some embodiments, the body 12 may be an expandable stent such as a self-expandable stent or a balloon expandable stent. Non-limiting examples of expandable stents include the Z-Stent® and the EVOLUTION® stent (Cook Medical Incorporated, Bloomington, Ind.). In some embodiments, the body 12 may be a non-expandable tubular stent. The proximal portion 14 of the body 12 may include an end portion 15 having an expanded outer diameter and the distal portion 16 may include an end portion 17 having an expanded outer diameter. In some embodiments, the body 12 may be a substantially straight tubular shape. The body 12 may include a coating or a sleeve 22 extending through and/or around the body 12 that is liquid impermeable so that liquid and nutrients flowing from the proximal portion 14 to the distal portion 16 or stomach contents from the distal portion 16 to the proximal portion 14 do not pass through a wall 24 of the body 12.

As shown in FIG. 1, the prosthesis 10 includes a valve 28 that may extend distal to the body 12. In some embodiments, the valve 28 may be contiguous with the coating or sleeve 22 and in some embodiments the valve 28 may be separately provided. The valve 28 includes a lumen 29 operably connected to the lumen 18 of the body 12. The valve 28 is configured to control fluid flow through the prosthesis 10. The valve 28 may be formed such that the valve 28 is closable on itself due to the shape of the valve 28 when the valve 28 is made as described below. The valve 28 is closable on itself forming a seal to prevent stomach contents from leaking into the mouth through the prosthesis 10, especially when a patient is in a prone position and when the pressure within the stomach is at standard atmospheric pressure. When the patient is standing, there is usually some pressure above atmospheric pressure within the stomach that can facilitate closure of the valve 28. However, when the patient is in a prone position, there may be no additional pressure in the stomach to facilitate closure of the valve 28 so the shape of the valve 28 helps facilitate closure of the valve 28 at standard temperature and pressure described below. In contrast, valves formed as a straight tubular configuration, having a cylindrical distal end or a conical distal end, do not close and form a seal at standard atmospheric pressure. These types of cylindrical and conical distal openings in the valve require additional pressure, such as from the stomach, in order to close and seal.

Referring to the embodiment shown in FIGS. 1 and 2, the valve 28 is operably connected to the body 12 and extends distally from the distal portion 16 of the body 12. In other embodiments, the valve 28 may be connected to the body 12 at any position along the body 12. By way of non-limiting example, the valve 28 may be attached anywhere on the distal end portion 17 of the body 12 including the distal portion of the end portion 17, the proximal portion of the end portion 17, to an inside surface or an outside surface of the end portion 17. In some embodiments, a proximal portion 30 of the valve 28 may be connected to the distal portion 16 of the body 12. In some embodiments, the proximal portion 30 of the valve 28 may be connected to the proximal portion 14 of the body 12. By way of non-limiting example, the valve 28 may be attached anywhere on the proximal end portion 15 of the body 12 including the distal portion of the proximal end portion 15 and to the proximal portion of the proximal end portion 15.

Figure 3:
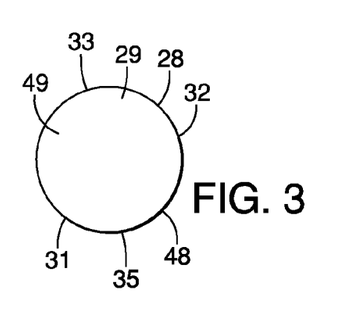
FIG. 3 is an end view of a valve of the embodiment shown in FIG. 1 in an open configuration.
Figure 4:
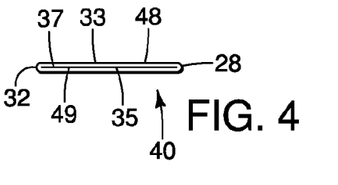
FIG. 4 is an end view of the valve of the embodiment shown in FIG. 1 in a closed configuration.
Figure 24:
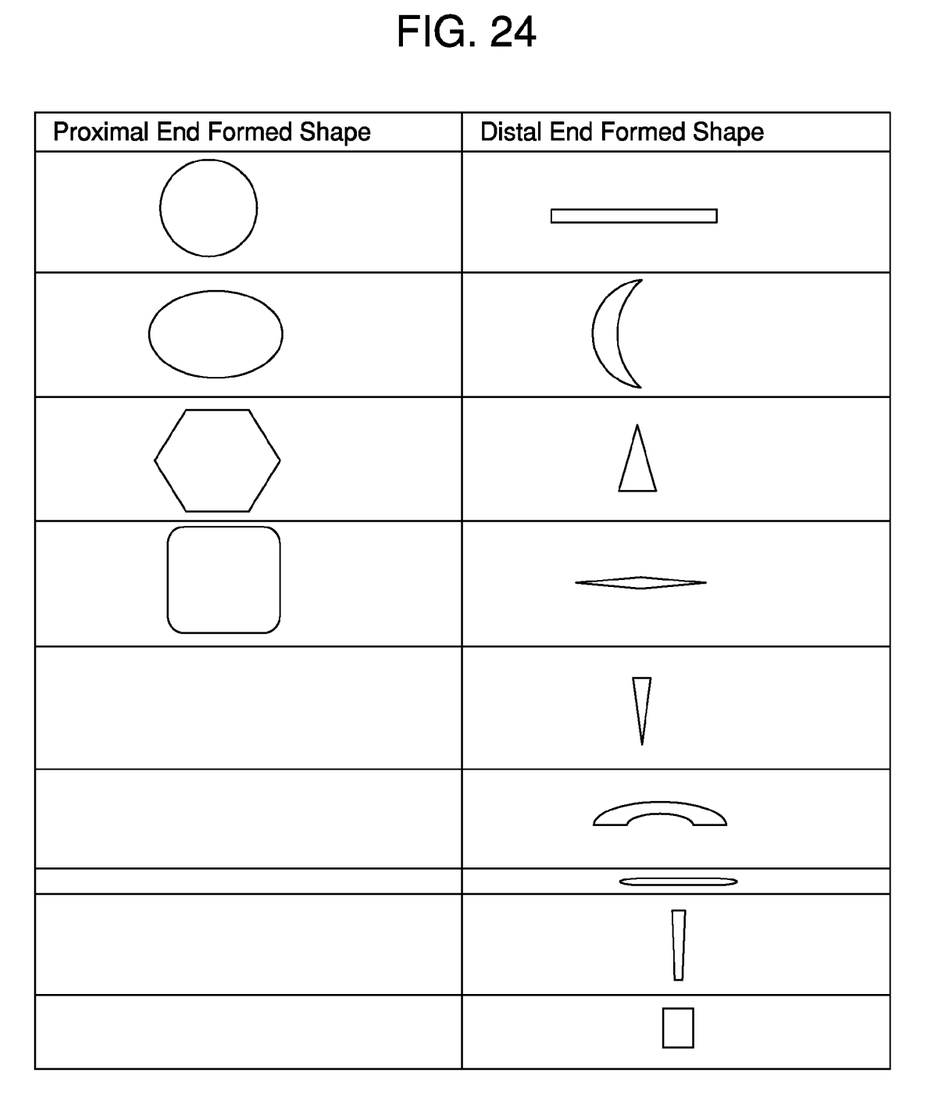
FIG. 24 illustrates exemplary formed shapes for the proximal end and the distal end of a valve in accordance with the present invention.

A distal portion 32 of the valve 28 may be configured to extend into the patient's stomach or other body lumen. The valve 28 has a closed configuration 40 shown in FIGS. 1 and 2 wherein an opening 49 in the distal portion 32 is closed on itself as acts as a protective barrier reducing the risk of stomach contents entering the valve 28 in a retrograde direction and subsequently leaking into the stent or esophagus of the patient even at standard temperature and pressure within the stomach and in the absence of external pressure within the stomach. An end view of the distal portion 32 of the valve 28 is shown in FIG. 4 in the closed configuration 40. In the closed configuration, a first portion 33 of a surface 31 of the lumen 29 contacts a second portion 35 of the surface 31 of the lumen 29 and forms a seal 37 at standard atmospheric pressure to prevent unwanted retrograde flow. An open configuration 44 is shown in FIG. 3 where the first portion 33 is spaced apart from the second portion 35. The valve 28 may be opened in response to a first pressure 50 flowing in the antegrade direction from the mouth to the stomach as described in more detail below. The opening 49 may open to a cylindrical shape. Additional exemplary shapes for the proximal and distal portions 30, 32 of the valve 28 are shown in the FIG. 24. As shown in FIG. 1, the valve 28 may taper from the proximal portion 30 to the distal portion 32 so that the diameter of the valve 28 decreases toward the distal portion 32 so that the cross-sectional area at the opening at the proximal portion 30 is greater that the cross-sectional area of the opening at the distal portion 32. In some embodiments, the valve 28 may flare outwards resulting in a wider distal portion 32 relative to the proximal portion 30 of the valve 28. The cross-sectional area of the opening at the distal portion 32 of this embodiment is greater than the cross-sectional area of the opening at the proximal portion 30 of the valve 28.

FIG. 2 shows the prosthesis 10 that has been rotated 90° relative to FIG. 1 so that a side view of the valve 28 is shown. The valve 28 may be formed to have the closed configuration 40 shown in FIG. 2 so that the valve 28 will close on itself as described in more detail below. In some embodiments, the valve 28 may be formed by molding, extrusion, electrospinning and the like. The shape of the valve 28 allows the valve 28 to close in the absence of external pressure (i.e. at standard temperature and pressure) rather than relying on pressure from within the stomach or body lumen to close the valve 28, for example when the valve is provided as a straight tube having a circular cross-sectional opening at the distal end that requires some amount of external pressure to close the valve. In some embodiments, the distal portion 32 of the valve 28 tapers from the widest portion at the proximal portion 30 to an intermediate portion 46 and to a distal end 48 of the valve 28 as shown in FIG. 2. The proximal portion 30 of the valve 28 has a similar size and shape to the distal portion 16 of the body 12, for example a generally circular or oval shape. In the embodiment shown in FIG. 2, the valve 28 tapers to a narrowed distal portion 32 so that the distal end 48 is flattened on itself and forms a seal as shown in FIG. 4. The valve 28 generally is in the closed configuration 40 in the absence of the first pressure 50 flowing in the antegrade direction or a second pressure 52 flowing in a retrograde direction that is greater than the first pressure 50.

Figure 5:
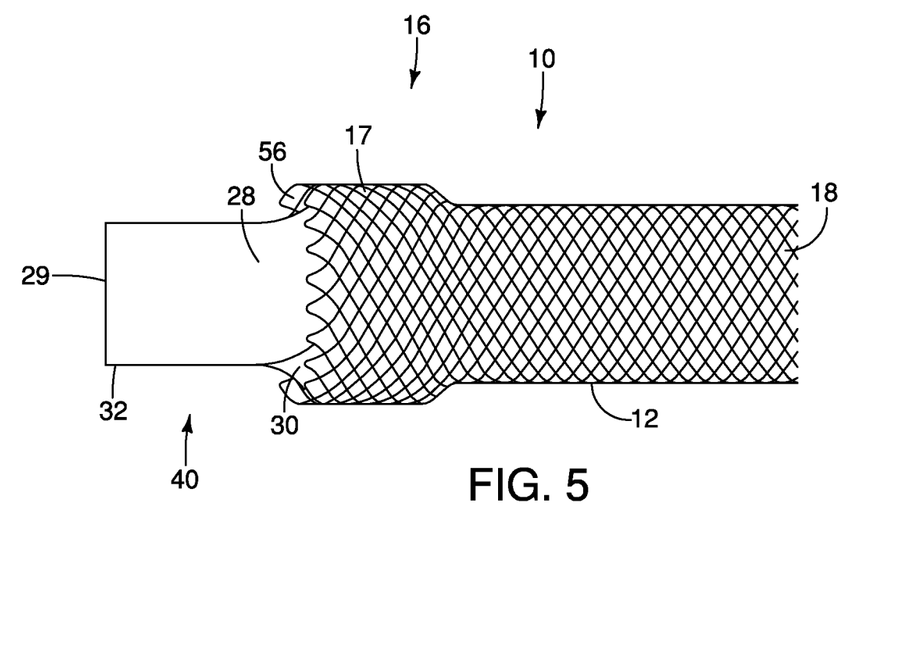
FIG. 5 is a partial side view of a prosthesis in accordance with an embodiment of the present invention.
Figure 6:
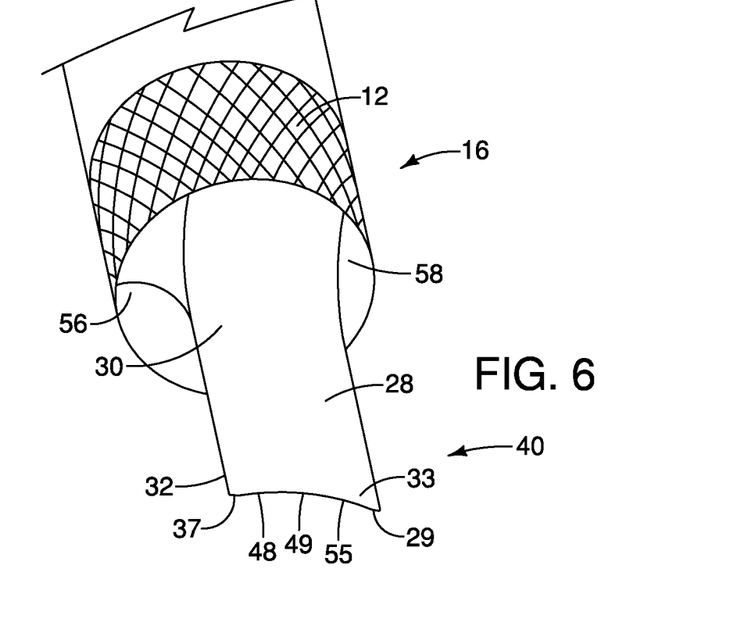
FIG. 6 is a partial perspective view of the embodiment of the prosthesis shown in FIG. 5 in a closed configuration.

FIG. 5 illustrates an embodiment of the prosthesis 10 having the valve 28 extending from a distal portion 16 of the body 12. The valve 28 may have a substantially continuous diameter from the proximal portion 30 to the distal portion 32 that extends from the distal portion 16 of the body 12 as shown in FIG. 5. The valve 28 may be connected to an interior portion 56 of the body 12 so that a proximal end 58 of the valve 28 is positioned within the body 12. The lumen 29 of the valve 28 is connected to the lumen 18 of the body 12 so that fluid can flow therethrough. The distal end valve 28 has the closed configuration 40 in the absence of the first pressure 50 and the second pressure 52 as can be seen in FIG. 6 wherein the distal end 32 is closed on itself so that fluid, such as stomach contents, cannot leak into the mouth of the patient even in the absence of pressure within the stomach. The first portion 33 of the inner surface 31 of the lumen 29 contacts the second portion 35 of the inner surface 31 to form the seal 37 as shown in FIG. 6.

Figure 7:
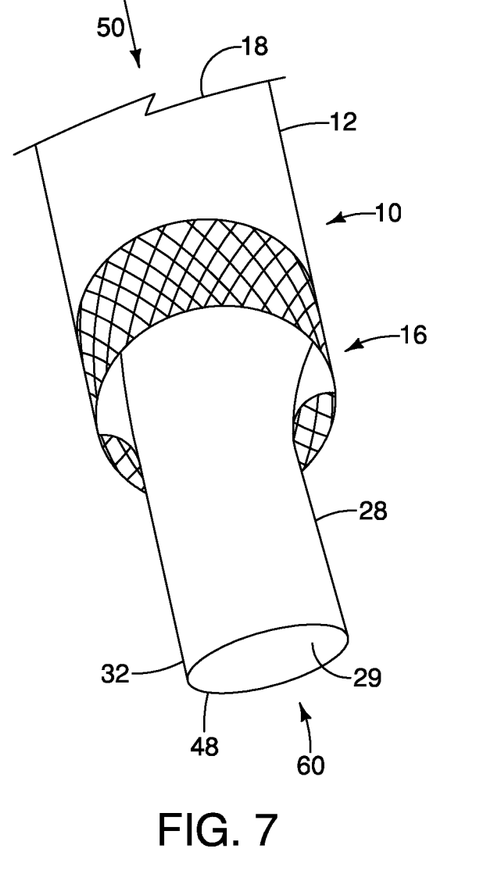
FIG. 7 is a partial perspective view of the embodiment of the prosthesis shown in FIG. 5 in an open configuration.
Figure 8:
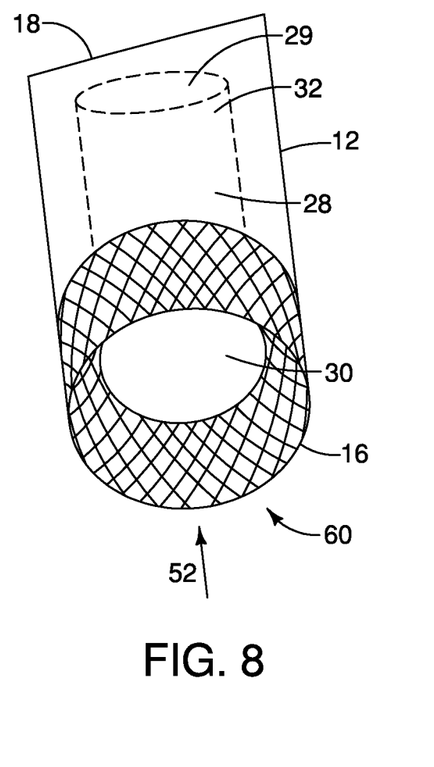
FIG. 8 is a partial perspective view of the embodiment of the prosthesis shown in FIG. 5 with the valve everted.

FIGS. 7 and 8 illustrate the valve 28 in an open configuration 60 in response to flow therethrough. As shown, fluid and nutrients can pass through the lumen 29 of the valve 28 in the antegrade direction (FIG. 7) or in the retrograde direction (FIG. 8). As shown in FIG. 7, the lumen 29 of the valve 28 is open in response to the first pressure 50 in the antegrade direction such as from fluid or nutrients passing from the mouth to the stomach. The distal end 48 of the valve 28 is open so that the diameter of the opening 49 in the distal end 48 is expanded in the open configuration 60 relative to the closed configuration 40. Once the first pressure 50 is removed, the valve 28 returns to the closed configuration 40 shown in FIG. 6.

FIG. 8 illustrates the valve 28 that has been everted in response to the second pressure 52 that is greater than the first pressure 50. For example, when the patient needs to belch or vomit, the valve 28 opens in response to the second pressure 52. The second pressure 52 pushes the valve 28 proximally to evert the valve 28 so that the distal end portion 32 of the valve 28 extends proximally. The valve 28 opens so that the second pressure 52 built up in the stomach may be relieved through the mouth. In the absence of the first or second pressure 50, 52, the valve 28 returns to the closed configuration 40 shown in FIG. 1. The valve 28 may be re-inverted so that the distal end portion 32 extends distally by the patient swallowing water. Depending on the length of the valve 28 and the length of the body 12, the valve 28 may evert so that the distal end portion 32 extends proximal to the proximal portion 14 of the body 12 or the valve 28 may extend proximally so that the distal portion 32 of the valve 28 is positioned within the lumen 18 of the body 12.

Figure 9:
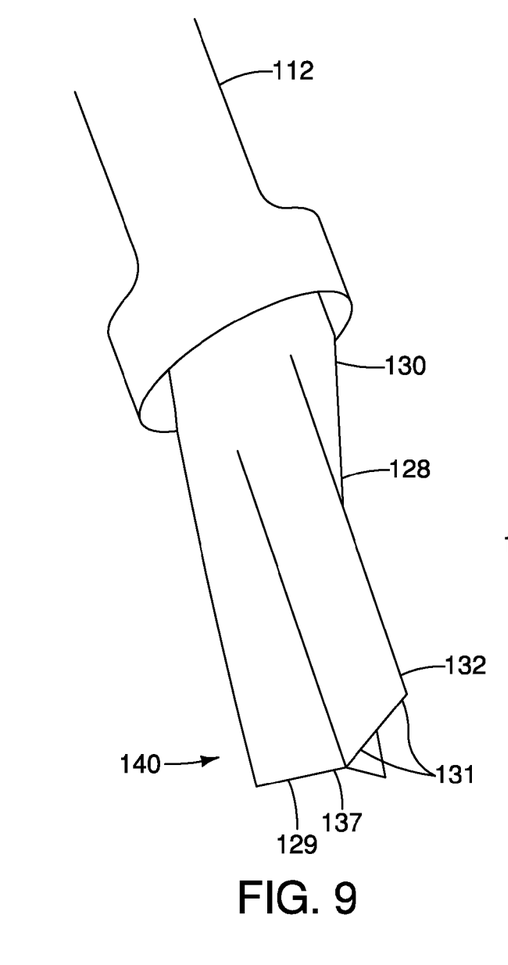
FIG. 9 is a partial perspective view of the prosthesis in accordance with an embodiment of the present invention.
Figure 10:
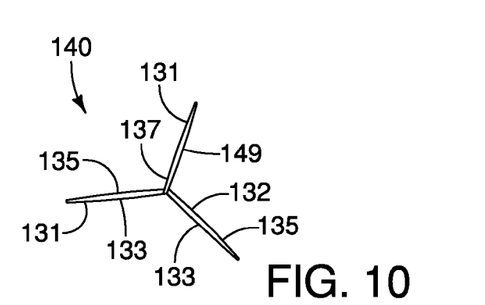
FIG. 10 is an end view of a valve of the embodiment shown in FIG. 9 in a closed configuration.
Figure 11:
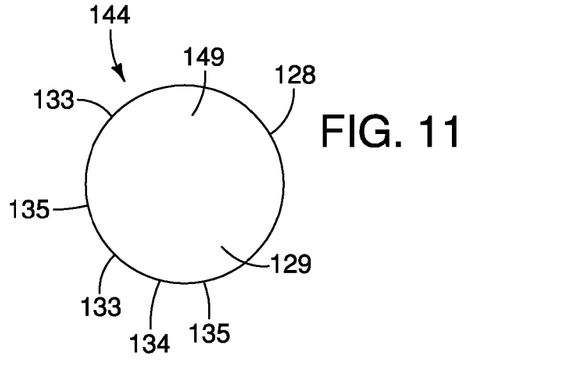
FIG. 11 is an end view of the valve of the embodiment shown in FIG. 9 in an open configuration.

An alternative embodiment of a prosthesis 110 is shown in FIGS. 9-11. The prosthesis 110 includes a body 112 that is similar to the body 12 described above. The prosthesis 110 also includes a valve 128 that is similar to the valve 28 described above except that the distal portion 132 is provided with a tricuspid shape that is normally in a closed configuration 140 shown in FIGS. 9 and 10. The valve 128 may include any of the features described for the valve 28 above. Similar to the valve 28, the valve 128 is closable on itself to form a seal 137 to prevent stomach contents from leaking into the mouth through the prosthesis, especially when a patient is in a prone position and when the pressure within the stomach is at standard pressure. The shape of the valve 128 helps facilitate closure of the valve 128 and formation of the seal 137 at standard pressure. A distal portion 132 of the valve 128 is configured to extend into the patient's stomach or other body lumen. The valve 128 has a closed configuration 140 shown in FIGS. 9 and 10 wherein an opening 149 in the distal portion 132 is closed on itself so that fluid and nutrients, such as stomach contents, cannot leak into the mouth of the patient even at standard pressure within the stomach. An end view of the distal portion 132 of the valve 128 is shown in FIG. 10 in the closed configuration 140 so that each cusp 131 is closed on itself and the opening 149 is closed. Each cusp 131 includes a first portion 133 of a surface 134 of a lumen 129 through the valve 128 and a second portion 135 of the surface 134 that contact each other in the closed configuration 140 to form the seal 137. An open configuration 144 is shown in FIG. 11 where the cusps 131 are opened and the opening 149 is formed in response either the first pressure 50 flowing in the antegrade direction or the second pressure 52 flowing in the retrograde direction. The valve 128 may open to a cylindrical configuration in the open configuration 144.

An alternative embodiment of a prosthesis 610 is shown in FIGS. 12-15. The prosthesis 610 includes a body 612 that is similar to the body 12 described above. The prosthesis 610 also includes a valve 628 that is similar to the valve 28 described above except that the distal portion 632 is provided with a u-shape configuration that is normally in a closed configuration 640 shown in FIGS. 12-14. The valve 628 may be formed so that the distal portion 632 remains closed and forms a protective barrier against reflux. A proximal portion 630 of the valve 628 may have a cylindrical shape and have a greater cross-sectional area than the distal portion 632. Compare FIG. 15A showing the proximal portion 630 with FIG. 15B showing the distal portion 632 of the valve 628 with the valve 628 open. The valve 628 may include any of the features described for the valves described above. Similar to the valve 28, the valve 628 is closable on itself to form a seal 637 to prevent stomach contents from leaking into the mouth through the prosthesis, especially when a patient is in a prone position. The formed shape of the valve 628 helps facilitate closure of the valve 628 and formation of the seal 637.

Figures 12, 13, 14, 15A, 15B, 15C:
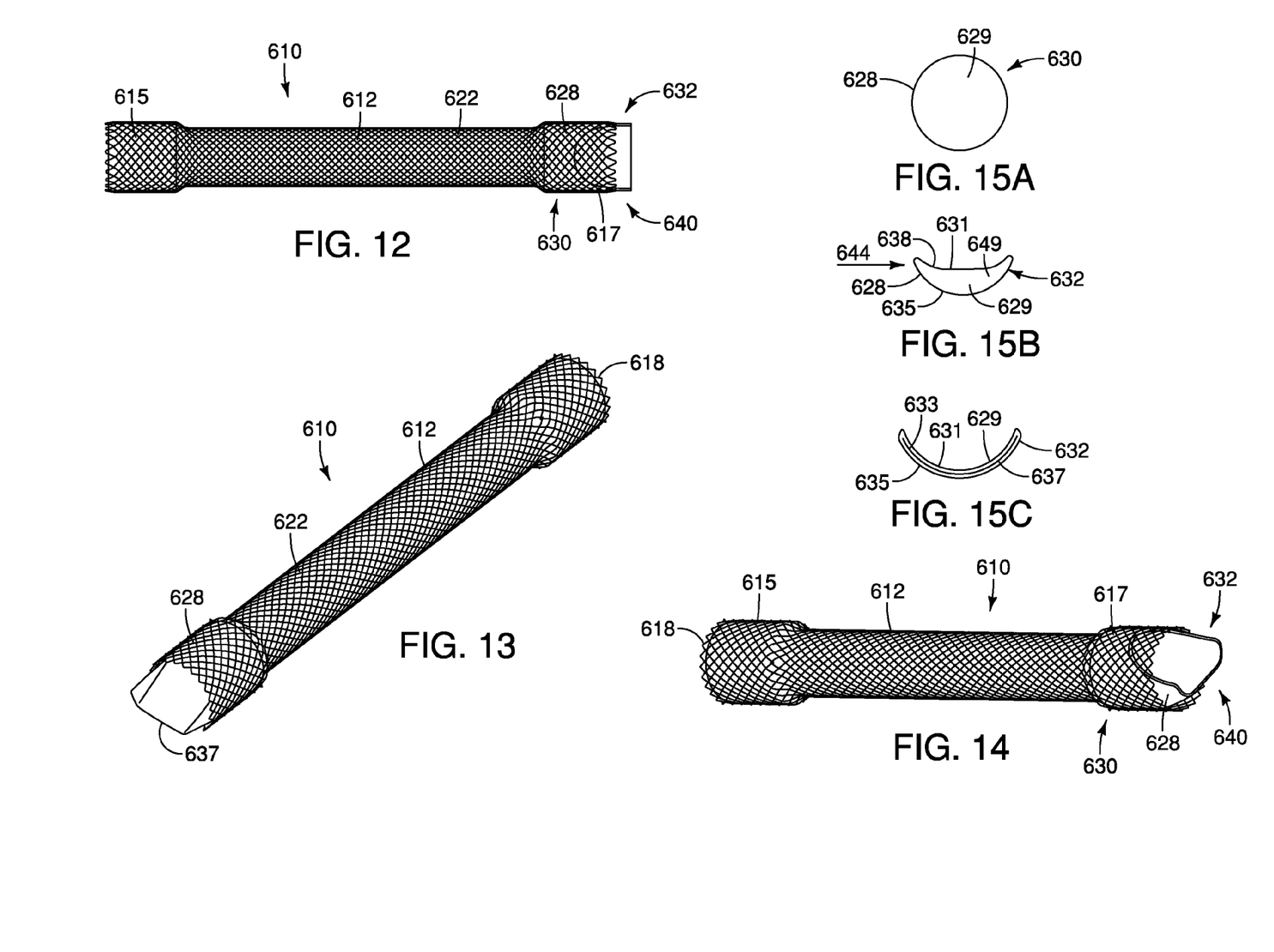
FIG. 12 is a side view of an embodiment of a prosthesis in accordance with an embodiment of the present invention.
FIG. 13 is a perspective view of the embodiment of the prosthesis shown in FIG. 12.
FIG. 14 is a perspective view of the embodiment of the prosthesis shown in FIG. 12.
FIG. 15A is a cross-sectional view of a proximal portion of a valve.
FIG. 15B is a cross-sectional view of a distal portion of the valve in an open configuration.
FIG. 15C is an end view of the distal portion of the valve shown in FIG. 15B in a closed configuration.

An end view of the distal portion 632 of the valve 628 is shown in FIGS. 15B and 15C. FIG. 15B illustrates the valve 628 in an open configuration 644 where a first portion 633 is spaced apart from a second portion 635 of the distal portion 632. In the closed configuration shown in FIG. 15C, the first portion 633 of a surface 631 of the lumen 629 contacts the second portion 635 of the surface 631 of the lumen 629 and forms a seal 637 at standard atmospheric pressure to provide the protective barrier to unwanted retrograde flow. The valve 628 may be opened in response to the first pressure 50 flowing in the antegrade direction from the mouth to the stomach. The opening 649 at the distal portion 632 of the valve 628 may open to smaller cross-sectional diameter than the proximal portion 630. The distal portion 632 of the valve 628 is configured to extend into the patient's stomach or other body lumen.

Figure 16:
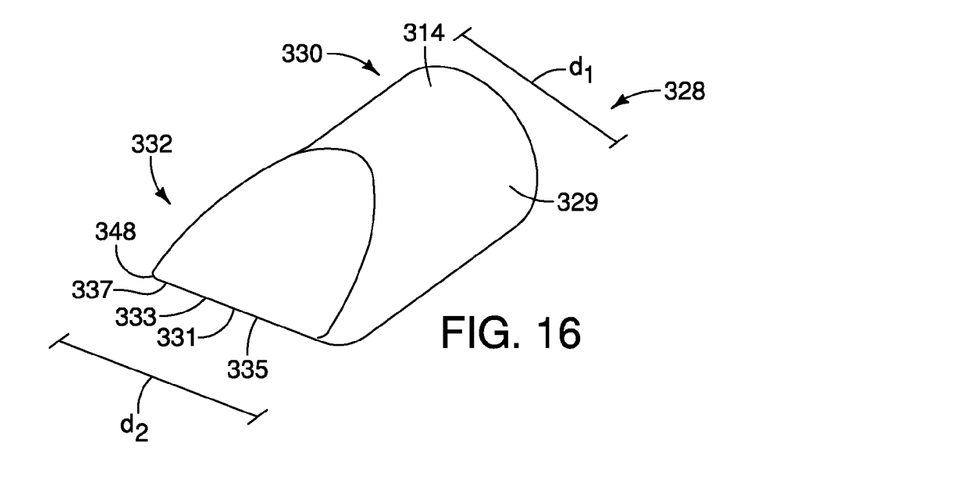
FIG. 16 is a perspective view of an embodiment of a valve.
Figure 17:
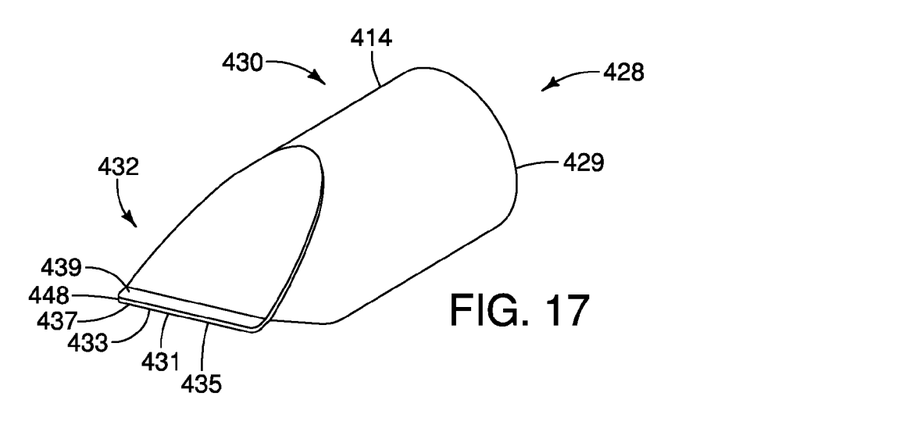
FIG. 17 is a perspective view of an embodiment of a valve.
Figure 18:
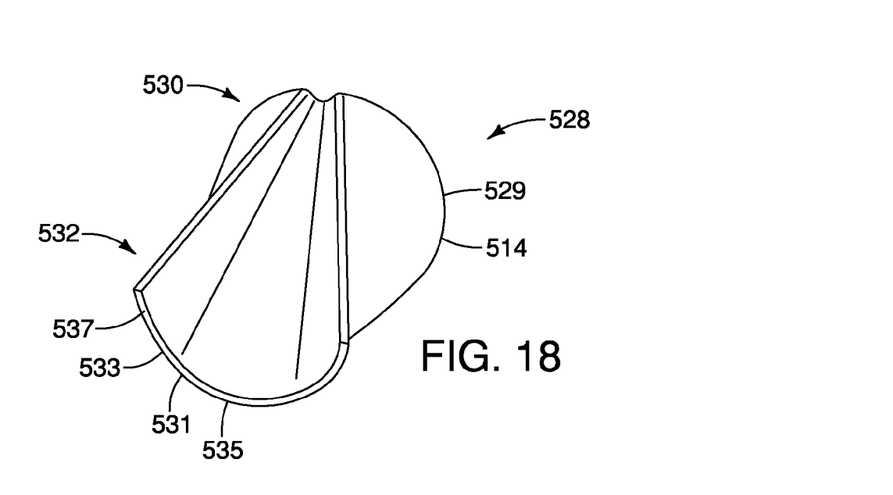
FIG. 18 is a perspective view of an embodiment of a valve.

FIGS. 16-18 illustrate exemplary embodiments of valves 328, 428, 528 in accordance with the present invention and are shown in the closed configuration. Each of the valve 328, 428, 528 may open to a generally circular shape as shown in FIG. 3 above in the presence of the first pressure 50 flowing in the antegrade direction. In some embodiments, the valves 328, 428, 528 may open to other shapes where the distal portion 332, 432, 532 has a smaller cross-sectional area in the open configuration that the proximal portion 330, 430, 530. The cross-sectional area of the distal portion of each of the valves 328, 428, 528 will depend on the shape that the valve is formed in the closed configuration. The valves 328, 428, 528 may be provided with a body 12 as described in the embodiments above. The valves 328, 428, 528 are similar to the valves described above except for the distal portion 332, 432, 532 as shown in FIGS. 12-14, respectively. The valves 328, 428, 528 may include any of the features described for the valves above. Similar to the valves described above, the valves 328, 428, 528 are closable on themselves to form a seal 337, 437, 537 to act as a barrier reducing the risk of stomach contents from leaking into the esophagus through the prosthesis, especially when a patient is in a prone position and when the pressure within the stomach is at standard pressure. The formed shape of the valves 328, 428, 528 helps facilitate closure of the valves and formation of the seal 337, 437, 537 at standard pressure. FIG. 16 illustrates an embodiment of the valve 328 where the distal portion 332 includes a first portion 333 of a surface 331 of a lumen 329 that contacts a second portion 335 of the surface 331 of the lumen 329 and forms the seal 337 at standard atmospheric pressure to prevent unwanted retrograde flow. The contact of the first portion 333 and the second portion 335 is at a distal end 348 of the valve 328. FIG. 17 illustrates an embodiment of the valve 428 where the distal portion 432 includes a first portion 433 of a surface 431 of a lumen 429 that contacts a second portion 435 of the surface 431 of the lumen 429 and forms the seal 437 at standard atmospheric pressure to prevent unwanted retrograde flow. The contact of the first portion 433 and the second portion 435 is at a distal end 448 of the valve 428 and extends proximally so that a flattened rectangular shaped region 439 is formed at the distal portion 432. FIG. 18 illustrates an embodiment of the valve 528 where the distal portion 532 is curved and may be U-shaped at a distal end 548. In some embodiments, the U-shape may extend from a proximal portion 514 to the distal end 548. As shown in FIG. 18, the U-shape may widen from the proximal portion 514 toward the distal end 548. The distal portion 532 includes a first portion 533 of a surface 531 of a lumen 529 that contacts a second portion 535 of the surface 531 of the lumen 529 and forms the seal 537 at standard atmospheric pressure to prevent unwanted retrograde flow. In some embodiments, a proximal portion 314, 414, 514 may have a diameter $d_1$ that is smaller than a diameter $d_2$ extending across the length of the distal portion 332, 432, 532. By way of non-limiting example, the diameter $d_1$ of the proximal portion 314 of the valve 328 may be about 20-30 mm and the diameter $d_2$ extending across the distal portion 332 may be about 25-40 mm. In some embodiments, $d_1$ may be about 25 mm and $d_2$ may be about 30 mm. In other embodiments, the diameter $d_1$ at the proximal portion of the valves described herein may be greater than the diameter $d_2$ of the distal portion. Where the shape of the distal portion of the valve is non-cylindrical, the cross-sectional area of the distal portion may be less than the cross-sectional area of the proximal portion.

Figures 19A, 19B:
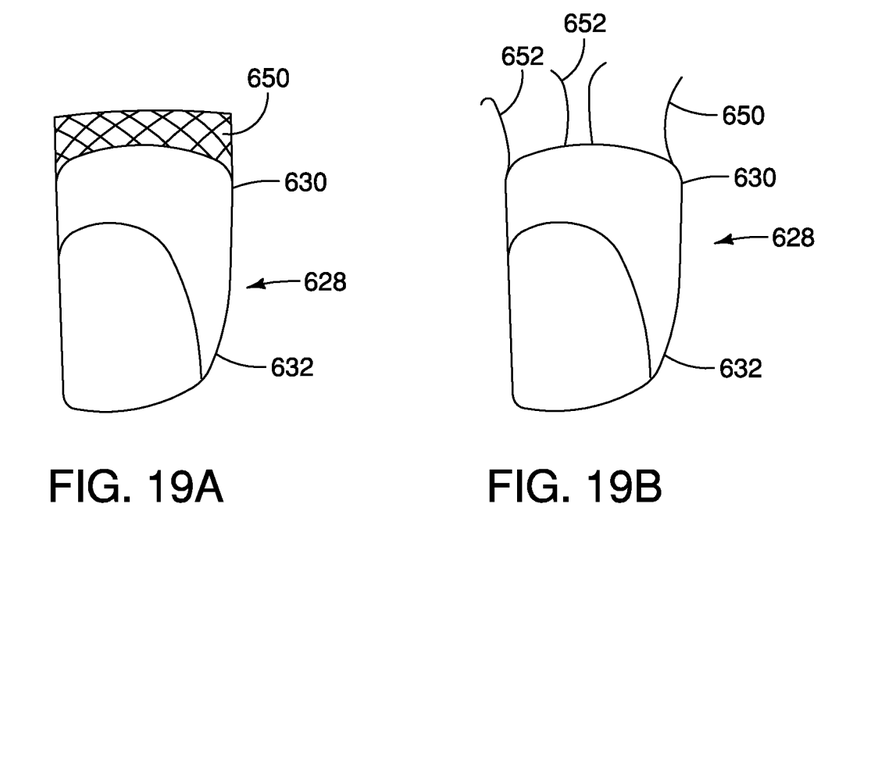
FIGS. 19A-C illustrate embodiments of a retrofit valve.
Figure 19C:
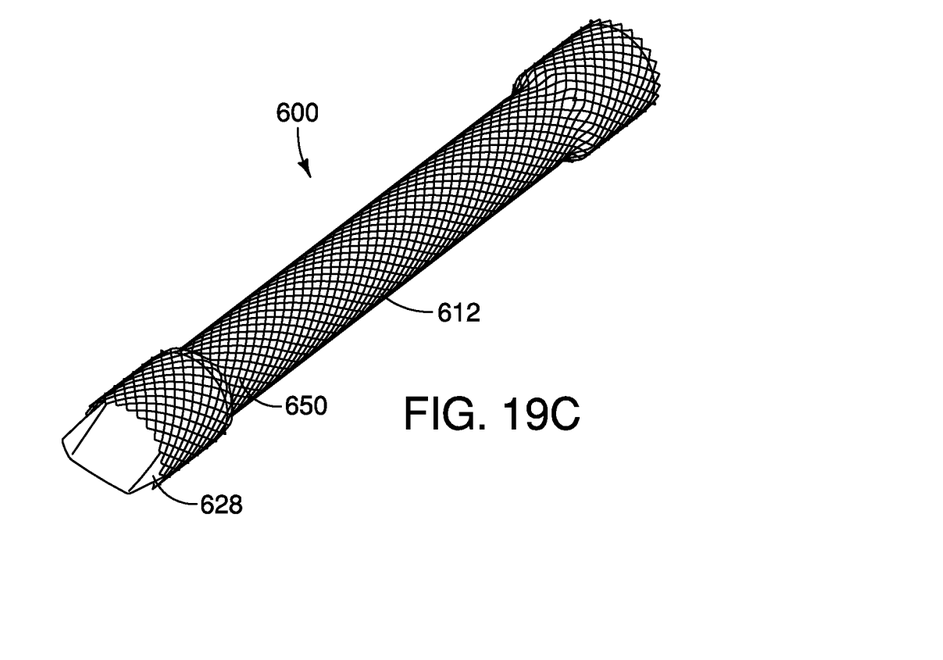
Figure 20:
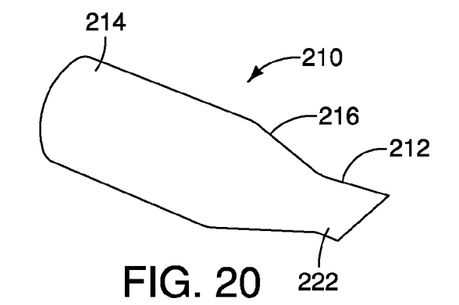
FIG. 20 is a perspective view of a mold for an embodiment of the valve in accordance with the present invention.
Figure 21:
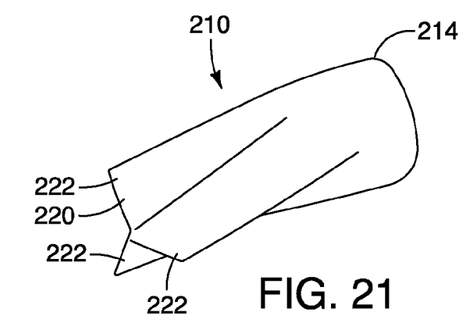
FIG. 21 is a perspective view of a mold for an alternative embodiment of the valve in accordance with the present invention.

In some embodiments, the valve may be retrofit into an existing body of a prosthesis that has already been positioned within a patient's lumen. By way of non-limiting example, the valve 628 is shown although any of the embodiments shown and described herein may be retrofit into an existing body such as a stent. The retrofit valves may have any of the features described and may also include an attachment member to attach the valve to the existing body. As shown in FIGS. 19A and 19B, the valve 628 may include an attachment member 650 that is configured to position the valve 628 within the body and hold the valve 628 within the body. The attachment member 650 may be connected to the proximal portion 630 of the valve 628 as shown, although other attachment positions for the attachment member 650 are also possible. By way of non-limiting example, the attachment member 650 may be provided as an expandable mesh that expands to conform to the shape of the lumen of the body into which the valve 628 is positioned as shown in FIG. 19A. In other embodiments, the attachment member 650 may be provided as a plurality of connectors 652 that are configured to connect to the stent to hold the vale 628 in position. Other methods and attachment members may also be used to secure the retrofit valve 628 to the body. An exemplary prosthesis 600 is shown in FIG. 19C where the valve 628 has been retrofit into the body 612 using the attachment member 650.

Figure 22:
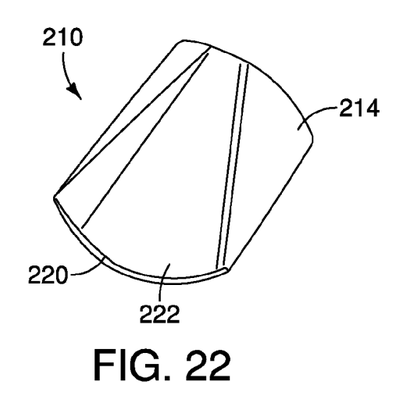
FIG. 22 is a perspective view of a mold for an alternative embodiment of the valve in accordance with the present invention.
Figure 23:
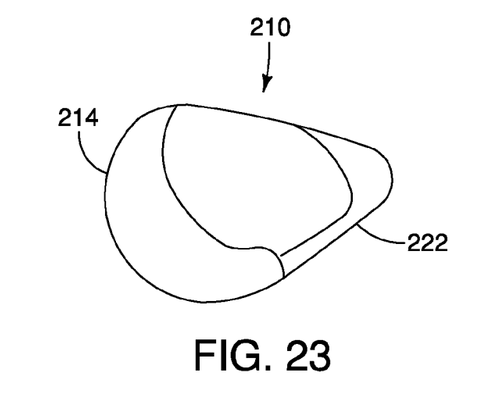
FIG. 23 is a perspective view of a mold for an alternative embodiment of the valve in accordance with the present invention.

FIGS. 20-23 illustrate exemplary mold forms 210 that may be used to form the valves described above. In some embodiments, the mold 210 may be provided having a tapered distal end 212 that forms the valve 28 having the closed configuration 40 shown in FIG. 1. The mold 210 shown in FIG. 15 includes a proximal portion 214 that may be sized and shaped so that the valve 28 formed thereon has the proximal portion 30 that is sized and shaped to fit with the body 12. In some embodiments, the mold 210 may include an intermediate portion 216 that tapers between the proximal portion 214 and the distal portion 212. The distal portion 212 of the mold 210 includes a substantially flattened or narrowed portion 222 that forms the first and second portions 33, 35 of the surface 31 of the lumen 29 so that when the mold 210 is removed and the valve 28 is formed, the first and second portions 33, 35 can contact each other and form the seal 37. In some embodiments, the cross-sectional area of the proximal portion 214 is greater than the cross-sectional area of the distal portion 212 of the mold 210 so that the valve 28 formed on the mold also has a greater cross-sectional area at the proximal portion 30 of the valve 28. The mold 210 shown in FIG. 21 may be provided having a tricuspid shaped distal end 220. The distal end 220 includes three substantially flattened portions 222. Similar to the embodiment described above, the first and second portions 133, 135 of the surface 134 of the lumen 129 can contact each other when the mold 210 is removed and form the seal 137. The distal end 220 allows the valve 128 that is formed to form the closed configuration 140 having the seal 137 at standard pressure. The mold 210 shown in FIG. 16 includes the proximal portion 214 that is sized and shaped to fit with the body 12. The molds 210 shown in FIGS. 22 and 23 illustrate a u-shaped distal portion 222 where the distal end 220 is narrower than the proximal portion 214. Any shape mold that includes a substantially flattened distal end portion that is configured to provide for contact of portions of the surface of the lumen once the mold is removed and allow for a seal to be formed in atmospheric pressure may be used. See exemplary proximal and distal end shapes for the valve in FIG. 24.

The valve described in the embodiments above may be made of a biocompatible material that will not substantially degrade in the particular environment of the human body into which it is to be placed. Possible materials include expanded polytetrafluoroethylene (ePTFE), Dacron, PTFE, TFE, PE, PET, polyolefins or polyester fabric, polyurethane, polysilicone, silicone, nylon, polyamides such as other urethanes, or other biocompatible materials. An exemplary material for the valve is a medical grade polyurethane material grade EG-80A material commercially known as TECOFLEX® polyurethane material (Thermedics, Incorporated, Woburn, Mass.) or medical grade silicone. In some embodiments, the material may be radiopaque to allow the position of the valve to be viewed by X-ray. In some embodiments, the valve may be made radiopaque using radiopaque ink or dusting the surface of the valve with a radiopaque powder or embedding the radiopaque material into the valve.

In some embodiments, a polymer material may be provided in a coating solution having the consistency required for dip coating the mold to form the valve. The valve may be prepared by dip coating the solution onto PTF mandrels. In some embodiments, the mandrels may be made from other materials such as anodized aluminum; glass; Dacron, mild steel and stainless steel. The number of coats applied can be used to develop the desired valve thickness. In some embodiments, a solution may be spray coated onto the mold forms to form the valve. In some embodiments where the polymer is spray or dip coated on to the mold, the mold may then be placed in an oven and cured at a high temperature. In some embodiments, the valve may be formed by electrospinning a polymer coating over the mold to form the valve membrane. The valve may also be formed using a heat shrink process, a blow molding process, extruding, molding, weaving or by heat forming a polymer film over the mold. In some embodiments, the valve may be formed by injection molding, dip coating, spraying, extruding, heat shrinking or balloon blowing technology. Other methods for forming the valve may also be used that allow the distal portion of the valve to be closed at standard pressure. The materials used to manufacture the components of the prosthetic devices described herein may be any materials known to one skilled in the art that are suitable for use in patients. By way of non-limiting example, the body may be formed from metals or polymers. Suitable exemplary metals include stainless steel and nitinol and the body may be woven or provided in a zig-zag configuration. In some embodiments, the body or portions thereof may be coated with silicone.

Figure 25:
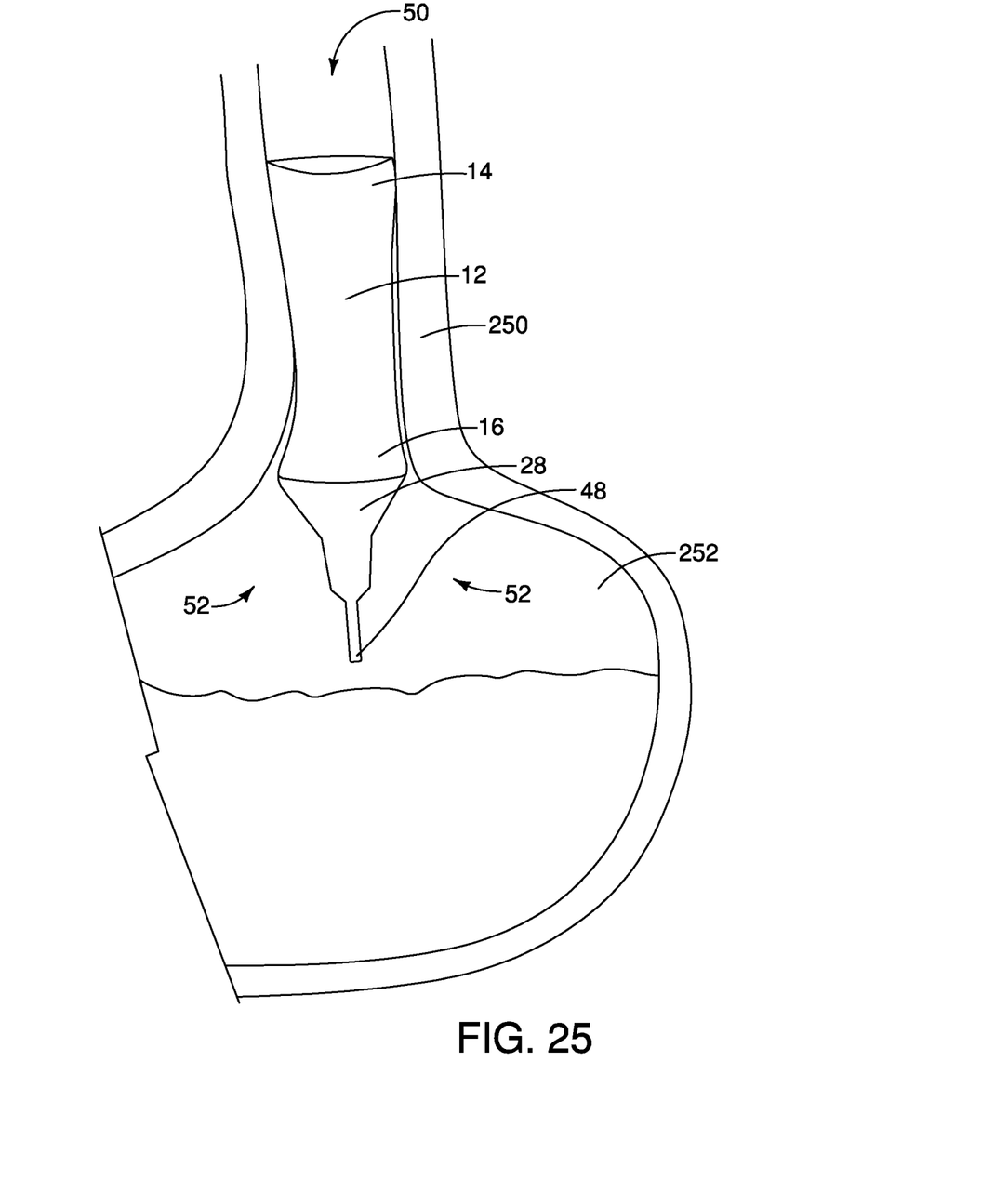
FIG. 25 illustrates an embodiment of a prosthesis positioned within the lower esophageal sphincter.
Figure 26A:
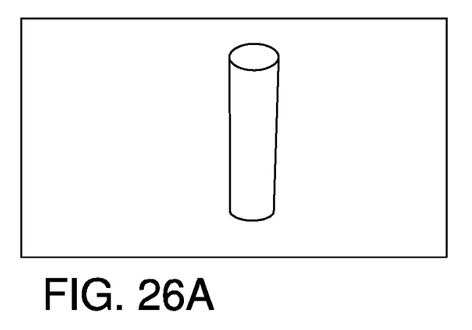
FIGS. 26A-26D illustrate shapes of the distal ends of valves.
Figure 26B:
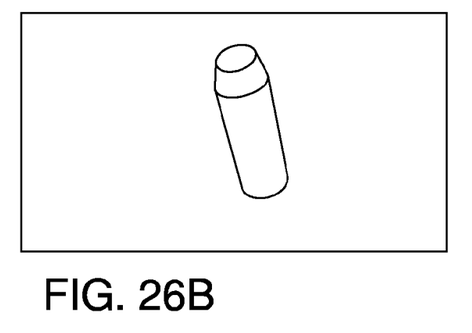
Figure 26C:
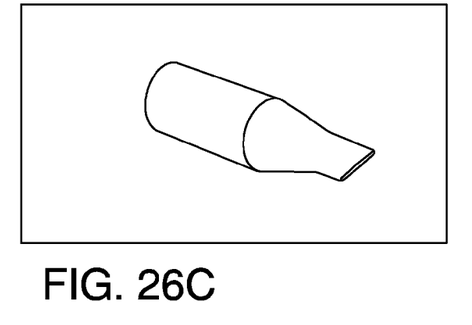
Figure 26D:
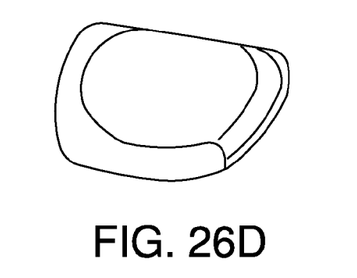

As shown in FIG. 25, the prosthesis 10 may be positioned in the lower esophageal sphincter 250. The proximal portion 14 of the body 12 may be positioned proximal to the esophageal sphincter 250. The distal portion 16 of the body 12 may be positioned so that the distal portion 16 and the valve 28 extend into the stomach 252. The valve 28 may extend any distance into the stomach 250 and remain closed in the absence of the first pressure and the second pressure and at standard pressure within the stomach or body lumen. The valve 28 is configured to open in response to the first pressure 50 and the second pressure 52.

In some embodiments, the length of the valve may be from about 10 mm to about 200 mm and in some embodiments from about 20 mm to about 120 mm. The length may vary and will depend on anatomy of the patient. In some embodiments, the diameter of the valve 28 may be from about 5 mm to about 50 mm and in some embodiments from about 8 mm to about 35 mm. In some embodiments by way of non-limiting example, the diameter of the proximal end of the valve may be about 18, 20, 23 or 25 mm. In some embodiments by way of non-limiting example, the diameter of the distal end of the valve may be about 10, 12, 15, 18, 20, 23 or 25 mm. In some embodiments, the diameter may change from the proximal portion to the distal portion so that the formed shape of the valve has a cross sectional area at the proximal portion of the valve that is greater than the cross sectional area at the distal portion and in some embodiments, the diameter may be constant. The thickness of the valve may also vary. In some embodiments, the valve may be preloaded in the body for delivery to the site within the patient to shorten so that the valve is at least partially positioned within the body. This delivery position for the valve will allow for a shorter end portion of the delivery system. This allows the physician to deploy the body in a more proximal position to reduce the risk of perforation within the stomach wall from the delivery system tip. The patient may drink a glass of water to release the valve from the body and extend the valve into the stomach. If the material used for the valve is susceptible to self-adherence, a coating sleeve material may be included that for example may be made of sugar that is coated onto or incorporated into the valve that will easily dissolve in the stomach. In some embodiments, a silicon oil or other oil, dusting the surface with particles or embedding the particles in the valve material may be used to prevent the material from self-adhering.

A test of some embodiments of differently shaped valve configurations is shown in Table I below. The shapes are shown in FIGS. 26A-26D and reflect the shape of the distal end of the valve at standard atmospheric pressure. Other shapes, such as the shapes shown in FIG. 24 may also be tested. The test illustrates the difference that the shape of the distal portion of the valve makes in having a valve that is closed at standard temperature and pressure. For the shapes tested, the diameter of the proximal end is 25 mm (cylindrical shape). Other diameters for the proximal and distal ends may also be used. By way of non-limiting example, the distal section of the valve may be designed to open to circular shape with a diameter ranging from 10-60 mm. In some embodiments, the distal section of the valve may be designed to open to other than a circular shape and to have a cross-sectional area that is smaller than the cross-sectional area of the proximal section. The thickness of the valve may vary from 0.0001"-0.0040". The length of the valve may vary from 0.5-6.0 cm. All valves were dimensionally equivalent. (STP standard temperature and pressure.)

TABLE I

| Shape | FIG. | Diameter (mm) | Proximal End Thickness (In.) (2 layer) | Distal End Thickness (In.) (2 layer) | Appearance @STP | Seal @STP |
|---|---|---|---|---|---|---|
| Cylinder | 19A | 25 | 0.003-0.0022 | 0.003-0.0022 | Open | No |
| Cone | 19B | 25 | 0.003-0.0022 | 0.003-0.0022 | Open | No |
| Taper | 19C | 25 | 0.0120 | 0.003-0.0022 | Closed | Sealed |
| U-Shaped | 19D | 25 | 0.003-0.0022 | 0.003-0.0022 | Closed | Sealed |

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A prosthesis for controlling flow through a bodily lumen, the prosthesis comprising:
a body having a proximal portion, a distal portion and a lumen extending therethrough;
a valve operably connected to the body, the valve having a proximal portion, a distal portion and a lumen extending through the valve, the valve lumen operably connected to the body lumen, the valve controlling flow through the prosthesis in a first direction and a second direction so that flow through the valve occurs in the first direction and the second direction with the valve in an open configuration; the valve having a distal end positioned distal to a distal end of the body, the distal end of the valve comprising a first portion of a surface of the valve lumen and a second portion of the surface that contact each other and form a seal in a closed configuration at atmospheric pressure, the seal consisting of the first portion and the second portion;
wherein the distal end of the valve is formed to have the closed configuration such that the first portion and the second portion of the surface of the valve lumen contact each other and the first portion and the second portion form the seal and the valve comprises a substantially U-shaped radial cross-section at the distal end of the valve in the closed configuration; and
wherein the distal end of the valve is configured to open in response to a pressure that is greater than atmospheric pressure;
and wherein the substantially U-shaped radial cross-section extends from the proximal portion of the valve to the distal end of the valve in the closed configuration.

2. The prosthesis of claim 1, wherein the valve comprises an attachment portion to retrofit the valve into the body that has been placed in a patient's lumen.

3. The prosthesis of claim 1, wherein the valve is formed on a mold.

4. The prosthesis of claim 1, wherein the valve comprises a tapered distal end.

5. The prosthesis of claim 1, wherein the valve comprises a cylindrically shaped proximal portion sized and shaped to fit with the body.

6. The prosthesis of claim 1, wherein the valve is tapered inward or tapered outward from the proximal portion to the distal portion of the valve.

7. The prosthesis of claim 1, wherein the proximal portion of the valve is positioned within the lumen of the body.

8. The prosthesis of claim 7, wherein the valve is configured to move to the open configuration in response to a second pressure that is greater than the first pressure.

9. The prosthesis of claim 1, wherein the valve is configured to move to an open configuration in response to the pressure comprising a first pressure in an antegrade direction wherein the first portion and the second portion of the surface are spaced apart.

10. The prosthesis of claim 9, wherein the valve is configured to at least partially evert so that the distal portion of the valve is proximal to the proximal portion of the valve in response to the second pressure.

11. The prosthesis of claim 1, wherein the valve comprises a curve along a longitudinal axis or a curve along a circumference of the valve.

12. The prosthesis of claim 1, wherein the distal end of the valve in the open configuration has a smaller cross sectional area than a cross sectional area of an opening in a proximal end of the valve.

13. A prosthesis for controlling flow through a bodily lumen, the prosthesis comprising:
a body having a proximal portion, a distal portion and a lumen extending therethrough;
a valve operably connected to the body, the valve having a proximal portion, a distal portion and a lumen extending through the valve, the valve lumen operably connected to the body lumen, the valve controlling flow through the prosthesis in a first direction and a second direction so that flow through the valve occurs in the first direction and the second direction with the valve in an open configuration; the valve having a distal end positioned distal to a distal end of the body, the distal end of the valve comprising a first portion of a surface of the valve lumen and a second portion of the surface that contact each other and form a seal in a closed configuration at atmospheric pressure, the seal consisting of the first portion and the second portion;
wherein the distal end of the valve is formed to have the closed configuration such that the first portion and the second portion of the surface of the valve lumen contact each other and the first portion and the second portion form the seal and the valve comprises a substantially U-shaped radial cross-section at the distal end of the valve in the closed configuration; and
wherein the distal end of the valve is configured to open in response to a pressure that is greater than atmospheric pressure;
and wherein the valve tapers from the proximal portion of the valve to the distal portion of the valve so that the substantially U-shaped cross section at the distal end of the valve is offset from a longitudinal axis extending through a center of the body.

* * * * *